United States Patent [19]
Lefkowitz et al.

[11] Patent Number: 5,166,073
[45] Date of Patent: Nov. 24, 1992

[54] MINIATURIZED SENSOR FOR IONIZING RADIATION

[75] Inventors: Steven M. Lefkowitz, Walnut Creek, Calif.; Mary A. Leugers; Steven J. Brownell; Deborah C. Helmer; Patrick E. Kastl; Ray Chrisman; Patrick W. Langvardt, all of Midland, Mich.

[73] Assignee: The Dow Chemical Company, Midland, Mich.

[21] Appl. No.: 347,692

[22] Filed: May 5, 1989

[51] Int. Cl.$^5$ .................................. H01L 70/00
[52] U.S. Cl. ............................ 436/57; 436/164; 422/58; 422/82.05; 128/634; 128/659; 128/662.06; 250/485.1; 356/73.1
[58] Field of Search ............ 422/58, 68.1, 82.05, 422/82.06, 82.09, 82.11; 436/57, 164; 128/633, 634, 659, 661.08, 662.06, 663.01; 250/483.1, 484.1, 485.1, 487.1; 356/73.1, 402, 412

[56] References Cited

U.S. PATENT DOCUMENTS

| | | | |
|---|---|---|---|
| 4,200,110 | 4/1980 | Peterson et al. | 422/58 |
| 4,265,249 | 5/1981 | Schindler et al. | 128/635 |
| 4,344,438 | 8/1982 | Schultz | 128/634 |
| 4,622,974 | 11/1986 | Coleman et al. | 128/634 |
| 4,682,895 | 7/1987 | Costello | 422/68.1 |
| 4,710,623 | 12/1987 | Lipson et al. | 128/634 |
| 4,752,141 | 6/1988 | Sun et al. | 374/161 |
| 4,765,339 | 8/1988 | Jones | 128/632 |
| 4,785,814 | 11/1988 | Kane | 128/634 |
| 4,788,436 | 11/1988 | Koechner | 250/485.1 |
| 4,800,886 | 1/1989 | Nestor | 128/634 |

OTHER PUBLICATIONS

Rheingold et al., "Surgical Catheterization of Hepatic Poital & Peripheral Circulations and Maintence in Pharmaeokinetic Studies", Journal of Pharm. Sci., vol. 71, No. 7/1982, pp.840-842.
Wakeley et al., "A Method for Preparing and Maintaining Rhesus Monkeys with Chronic Venous Catheter", Behavior Research Methods & Instrumentation, 1974, vol. 6, No. 5, pp. 329-331.
Barazal et al., "Implentation and Stabilization of Indnelling Vascular Catheter in the Rabbit", J. Appl. Physiol. 29 CU: pp.113-114, 1970.
Michael F. Sepaniak, "The Chemical Use of Laser-Excited Fluorometry", Clinical Chemistry, 31, 671 (1985).
Bruce J. Tromberg et al., "Development of Antibody-Based Fiber-Optic Sensors for Detection of a Benzo[a]pyrene Metabolite", Analytical Chemistry, 60, 1901 (1988).
Schram et al., "Determination of Tritium and Carbon-14 in Aqueous Solution with Anchracene Powder", Anal. Biochem 3, (1962), 68-72.
Lauber, "Development of Miniaturized Solid State Detectors for the Measurement of Beta & Gamma Radiation in Superficial and Deep Parts of Living Tissue", Nucl. Instr. and Meth. 101 (1972) 545-550.
Swenth et al., "Biomedical Probe Using a Feber-Optic Coupled Scintillator", Medical Physics 3, (1976), 109-112.

Primary Examiner—Robert J. Warden
Assistant Examiner—Lyle A. Alexander

[57] ABSTRACT

The invention is an optical sensor useful for the detection of ionizing radiation emitted from an analyte in a fluid. The sensor is composed of a permeable scintillator having a high surface area to scintillator volume ratio and an optical waveguide located in working relation to the scintillator to collect light photons generated in response to an ionizing radiation source. The sensor is especially useful for biomedical applications. Increased sensitivity allows for miniaturization and implantation in a blood vessel of a small experimental animal.

30 Claims, 1 Drawing Sheet

MINIATURIZED SENSOR FOR IONIZING RADIATION

FIELD OF THE INVENTION

The present invention relates to an optical sensor and method for the detection of ionizing radiation emitting analytes in fluids. It more specifically relates to an implantable biomedical sensor and method for monitoring radionuclide-labelled analytes in biological fluids.

BACKGROUND OF THE INVENTION

The technique of labelling compounds with radionuclides is widely used to monitor the concentration of analytes in biological tissue and fluids. An analyte, e.g., a compound to be analyzed, is synthetically prepared or otherwise labelled with a radionuclide. The labelled analyte is administered to an animal and the level of radioactivity is measured in a body fluid, such as blood, as a function of time. These measurements can provide, for example, estimates of the biological half-life, the absorption rate, the steady state concentration in body fluids and the elimination rate of the analyte and any metabolites resulting therefrom. When these estimates are evaluated in conjunction with other data, such as physiological parameters, they provide insight as to the dosage levels which are efficacious or toxic.

Currently, monitoring the bloodstream concentration of a labelled analyte is a tedious, labor-intensive task with limited time resolution. The labelled analyte is introduced into an experimental animal and blood samples are extracted at various subsequent time intervals. The samples are then analyzed for radioactive content by conventional scintillation counting techniques. This in vitro method is prone to be cumbersome, time-consuming and insensitive. Additionally, if the experimental animal is small, such as a rat or a mouse, the number of samples that can be withdrawn from the animal is limited.

The above mentioned problems and limitations can be substantially alleviated by implanting a "real time" sensor into the bloodstream of the animal. An implantable sensor detects the labelled analyte in vivo, thus eliminating the need to withdraw blood samples. A sensor which is useful for detection of in vivo radiation must be small, compatible with living tissue and of adequate sensitivity to detect low levels of radiation. Biological research utilizing a large experimental animal, such as a dog, will preferably be designed to utilize an analyte which emits low enough levels of radiation to provide a dosage of less than about 2 millicuries (mCu). Research involving a small animal, such as a rat, will preferably be designed to provide a dosage of less than about 1 mCu in order to preserve the viability of the animal.

Miniaturized semiconductor probes for in vivo measurement of beta and gamma radiation are disclosed by Lauber, *Nuclear Instruments and Methods* 101 (1972) 545–550 Semiconductor sensor devices convert radiation energy directly into electrical current. Low levels of radiation result in low current levels at which semiconductor sensors are susceptible to electrical interference, e.g., noise.

Sensors which use optical methods to detect radiation do not suffer from the same type of signal to noise insufficiencies which effect semiconductor sensors at low radiation levels. Typical optical sensors use a scintillating medium to convert radiation energy into light energy. The light energy is then coupled to an appropriate electro-optical system via an optical waveguide. Swinth, et al., *Medical Physics* 3 (1976) 109–112 discloses a sensor comprising a thallium-doped sodium iodide crystal surrounded by a diffuse reflector encased in an aluminum shell. Sensors of this design are limited to relatively large diametric proportions in order to assure adequate sensitivity at low radiation levels. Thus implantation into blood vessels is impractical.

It would be highly desirable to provide an in vivo sensor which is sensitive to low levels of radiation, non-toxic and of small enough proportion to be implantable in a blood vessel of any animal, even a small experimental animal such as a rat.

SUMMARY OF THE INVENTION

One aspect of the present invention is a sensor for determining the concentration of an ionizing adiation emitting analyte in a fluid comprising:

(a) a scintillator having a high surface area to scintillator volume ratio and permeability to said fluid: and (b) an optical waveguide in working relation with said scintillator to collect light photons generated by said scintillator in response to an ionizing radiation source.

Another broad aspect of the invention is a method for determining the concentration of an ionizing radiation emitting analyte in a fluid comprising the sequential steps of:

(A) inserting a sensor into the medium, wherein the sensor comprises:

(a) a scintillator having a high surface area to scintillator volume ratio and permeability to said fluid: and (b) an optical waveguide in working relation with said scintillator to collect light photons generated by said scintillator in response to an ionizing radiation source:

(B) collecting the light photons from the scintillator through the waveguide:

(C) measuring the number of the light photons per unit time and relating the measured number to a known standard to determine the concentration of the analyte in the fluid.

The sensor of the present invention demonstrates high sensitivity and therefore the sensor can be very small and still be effective, especially in detection of beta radiation. In another embodiment the sensor also includes a semipermeable membrane which separates the scintillator from the fluid. This embodiment allows for chemical selectivity, selectivity as to particle size, as well as, biocompatibility. These advantages render the present invention uniquely suitable for application in biological research and diagnosis, especially as an implantable sensor in the blood vessels of small experimental animals.

DETAILED DESCRIPTION

Figure 1:
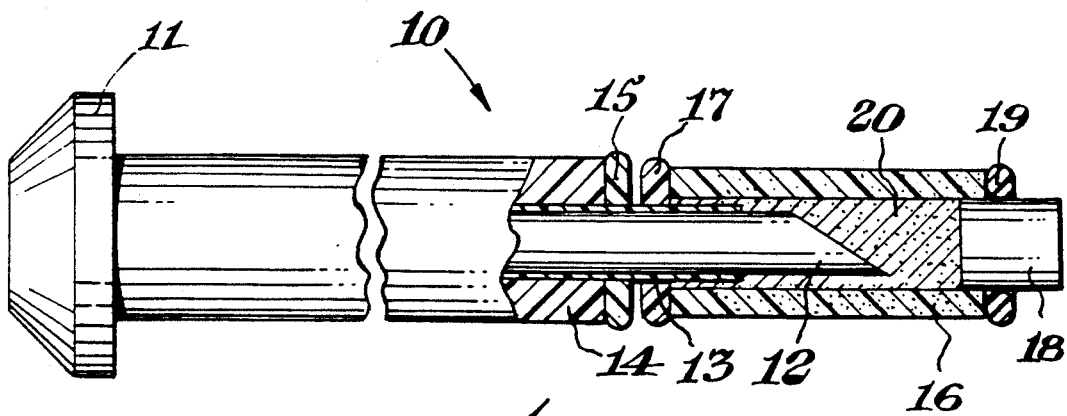
FIG. 1 depicts a cross-sectional view of an embodiment of a sensor of the present invention.

The term "high surface area to scintillator volume ratio" as used in this application means that the scintillator of the invention sensor has sufficient surface area per scintillator volume to yield a sensitivity to ionizing radiation in a fluid of from about $2.5 \times 10^3$ to about $1 \times 10^8$ counts per minute per disintigrations per minute per microliter per cubic meter of scintillator ($cpm/dpm/\mu l/m^3$).

"Ionizing radiation" is herein defined as particles or photons that have sufficient energy to produce ionization upon contact with the scintillators of the present invention. The ionization is sufficient to cause photons of light to be emitted by the scintillator. Ionizing radiation includes alpha particles, beta particles, gamma rays and x-rays, among others.

"Analyte" is herein defined to be a compound which is capable of being analyzed by radiotracer methods. It is normally a compound which has been tagged with an ionizing radiation source such as an alpha emitter, a beta emitter or a gamma emitter.

Analytes can be alpha radiators such as, for example, compounds labelled with salts or radicals of $^{144}Nd$, $^{147}Sm$, $^{149}Sm$, $^{152}Gd$, $^{174}Hf$, $^{190}Pt$, $^{192}Pt$, and $^{232}Th$. Preferably, alpha radiating analytes can be neodymim chloride-$^{144}Nd$, samarium sulfate-$^{147}Sm$, gadolinium nitrate-$^{152}Cd$, hafnium oxide-$^{174}Hf$ and platinic chloride-$^{190}Pt$.

Analytes can also be beta radiators such as, for example, compounds labelled with salts or radicals of $^3H$, $^{14}C$, $^{22}Na$, $^{24}Na$, $^{32}P$, $^{35}S$, $^{36}Cl$, $^{42}K$, $^{45}Ca$, $^{51}Cr$, $^{52}Mn$, $^{59}Fe$, $^{60}Co$, $^{65}Zn$, $^{82}Br$, $^{131}I$ and $^{132}I$. Preferably, beta radiating analytes can be water-$^3H$, 1-methoxy-2-propanol-$^{14}C$, sodium chloride-$^{22}Na$, sodium ethoxide-$^{24}Na$, phosphoric acid-$^{33}P$, 2-mercaptoethanol-$^{35}S$, chloroacetic acid-$^{36}Cl$, potassium iodide-$^{42}K$, potassium zinc acetate-$^{65}Zn$, N-bromosuccinimide-$^{82}Br$, cobalt carbonate-$^{60}Co$ and iron pentacarbonyl-$^{59}Fe$.

Gamma radiators can also be used as analytes These include, for example, compounds labelled with salts or radicals of $^{54}Mn$, $^{55}Fe$, $^{57}Co$, $^{75}Se$ and $^{125}I$. Preferably, gamma radiating analytes can be manganese bromide-$^{54}Mn$ and 5-iodo-2'-deoxyuridine-$^{125}I$.

Analytes can be compounds which when ingested or administered to an animal become endogenous. These analytes can be radiotracers such as labelled synthetic reagents, labelled biosynthetic substrates, labelled nucleic acids or other macromolecules. For example, thymidine, polypeptide hormones and steroids can be labelled and made endogenous in order to study anticancerous drugs, analgesic drugs and contraceptive drugs. Labelled neurotransmitters, such as norepinephrine, dopamine and serotonin can be labelled and made endogenous to be used to study the pharmacodynamics of such drugs as neuroleptics, antianorectics, antiparkinson and antihypertensive drugs.

A great number of drugs such as local anesthetics, antifibrillating agents and antiepileptic agents effect cell membranes and their permeability to ions, e.g., sodium (Na) and potassium (K). The movement of these ions can be followed using analytes labelled with $^{24}Na$ and $^{42}K$ Cardiotonic drugs affect the distribution of calcium which can be traced using analytes labelled with $^{45}Ca$. Phosphate ions which are of major importance in the phosphorylation processes in animal tissue can be studied with the use of analytes labelled with $^{32}P$. The action of the drugs on blood flow can be studied with $^{86}Rb$-labelled analytes, $^{14}C$- or $^3H$-labelled antipyrin or radionuclide labelled microspheres such as microspheres labelled with $^{131}I$, microspheres labelled with $^{51}Cr$ and/or microspheres labelled with 87mSr.

The sensor of the present invention comprises a scintillator having a high surface area to scintillator volume ratio and permeability to the fluid to be monitored, and also a waveguide, placed in working relation with the scintillator to collect light photons generated by the scintillator in response to an ionizing radiation source.

In one embodiment, the sensor of the present invention further comprises a semipermeable membrane which encloses the scintillator.

The semipermeable membrane is permeable to the analyte, of sufficient strength to support the scintillator when the scintillator is formed of particulate material, and largely impermeable to unwanted macromolecular components. For example, when the fluid is blood, it is desirable to exclude macromolecules such as serum albumin and red blood cells from the proximity of interaction between the analyte and the scintillator.

For analysis of non-gaseous labelled analytes, preferred membranes are "ultrafiltration membranes" having a selectable molecular weight cut-off range of from about 5,000 to about 100,000. The membranes can, for example, be cellulose acetate, polyvinylidene fluoride, polytetrafluoroethylene, copolymers of acrylonitrile/-vinylpyrrolidone, polyamideimide, polysulfone, polyamide, hydrophilic polyolefin, copolymer of acrylonitrile/methallyl sulfonate, and sulfonated polysulfone.

For analysis of gaseous analytes i.e., labelled carbon dioxide, membranes can, for example, be selected from the group consisting of silicone rubber, microporous polyolefin, a polyfluorocarbon such as polytetrafluoroethylene, and combinations thereof.

The sensor of the invention can further comprise a reflecting surface positioned with respect to the optical waveguide and the scintillator in a manner such that the intensity of the light photons which are exposed to the optical waveguide is substantially increased.

Preferable waveguides comprise optical fibers. The optical fibers may be polymeric, inorganic or a combination of both. Among others, polymeric optical fibers can be fibers having a core of poly(methyl methacrylate) and having a cladding of a fluorocarbon polymer. The fibers can also have a core of polystyrene and a cladding of poly(methyl methacrylate). Inorganic optical fibers can be, for example, fibers having a core of glass, quartz or silica, and a cladding of a flourocarbon polymer or poly(methyl methacrylate).

The scintillator can be any substance with a high surface area to scintillator volume ratio that can be made permeable to the analyte and is capable of converting the ionizing radiation into photons of light which can be detected by the sensor of the present invention. The scintillator should not be unduly degradable by the analyte, the fluid or any other substances that may permeate the scintillator. The scintillator can be incorporated in or be used in the form of an openly cellular composition such as a foam or a sponge. In another embodiment, the scintillator can comprise particles which are contained within a semipermeable membrane.

In an embodiment in which the scintillator is particulate, the particles can be functionally defined as small enough to give a high surface area to scintillator volume ratio, but adequately large enough to allow for loose packing of the particles. Loosely packed particles allow for the rapid and efficient intermingling of analyte with particles, resulting in improved sensor response time. For example, the particles can be roughly spherical, of irregular configuration or of crystalline shape.

Scintillators may be inorganic, organic or a combination thereof. The scintillator is selected from the group consisting of inorganic crystals, inorganic amorphous solids, organic crystals, organic plastics and combinations thereof. The choice of a scintillator depends on the type of ionizing radiation being detected. For example, for the detection of gamma radiation a scintillator comprising inorganic crystals, such as thallium activated sodium iodide crystals can be used. On the other hand, organic crystal scintillators are most commonly employed for the detection of ionizing radiation such as alpha and beta particles.

Inorganic crystal scintillators can be alkali metal halide crystals activated by the inclusion of a dopent such as thallium, indium, tin, silver, copper, nickel, antimony and lead, among others. These dopents are added in a concentration in the range of about 0.05 mole percent to about 5 mole percent. Preferable crystals include NaI(Tl), NaBr(Tl), KBr(Tl), KI(Tl), KCl(Tl) and the like.

Inorganic amorphous solid scintillators can be zinc sulphide, cadmium sulphide, zinc selenide and cadmium selenide, either neat or doped with about 0.05 percent to 5 mole percent of silver or other ions: calcium tungstate, cadmium tungstate, zinc tungstate; a variety of silicates, e.g., borosilicates and phosphate glasses doped with cesium, samarium, copper, lead, europium, thallium, uranium, tin and manganese, in the range of about 0.05 mole percent to about 5 mole percent; and phenyl borazole, boron nitride or boric acid.

Plastic scintillators comprise a polymeric matrix in combination with at least one scintillator. The scintillator can be added to a monomeric mixture before the polymerization proccess or added after polymerization to a polymer or copolymer using methods such as solution blending or melt blending. Among the polymeric matrices can be poly(styrene), e.g. poly(p-ethyl styrene), poly(p-methyl styrene), poly(2,4-dimethyl styrene), poly(3,4-dimethyl styrene) and poly(p-n-butyl styrene): poly(vinyl toluene): poly(vinyl naphthalene): poly(vinyl anthracene): poly(methyl methacrylate) and the copolymers and blends thereof. The polymeric matrix can be a plastic foam. The above mentioned scintillators and mixtures of scintillators are commonly added to the matrix material in the range of 0.1 weight percent to about 10 weight percent based on the weight of the polymer.

Scintillators which are preferably useful for the present invention are organic crystals having a plurality of aromatic rings. The more preferred polynuclear aromatic scintillators are condensed polynuclear hydrocarbons or heterocyclic compounds having 3 to about 6 aromatic rings. The term, "condensed", as employed herein means that at least two of the rings have carbon atoms in common. These polynuclear aromatic compounds have at least two aromatic rings which include, for example, anthracene, e.g., 1,2,5,6-dibenzanthracene: picene: naphthacene: naphthalene, e.g., diphenyl naphthalene, beta-methyl naphthalene, dimethyl naphthalene: pentaoene: hexacene: phenanthrene, e.g., 2,3,6,7-dibenzphenanthrene, fluoranthene; chrysene pyrene: fluorene, e.g., dibenzofluorene: carbazole, e.g., naphthophenocarbazole: diphenylene oxide and mixtures of the aforesaid compounds. The most preferred scintillators are anthracene, phenanthrene, fluoranthene, naphthacene, fluorene and carbazole.

The foregoing list of scintillators is not intended to be limiting since any scintillator which can function in a state to provide a high surface area to scintillator volume ratio and is permeable can be employed.

A preferred sensor embodiment uses particulate anthracene as the scintillator. Anthracene scintillates in the presence of beta radiation. Anthracene particles are formed into a loosely packed column within a semipermeable membrane in proximity to the distal end of an optical waveguide. When the sensor is placed in a fluid, e.g., blood, containing a $^{14}C$ labelled analyte, the semipermeable membrane allows the beta emitting analyte to come into direct contact and intermingle with the particles of the scintillator, while excluding cellular or macromolecular biological components. Thus, the emitted beta radiation can excite the scintillator with little attenuation and the resulting photons of light are efficiently coupled into the waveguide. The photons are then focused onto a conventional photon counting apparatus and the concentration of the analyte in the fluid is determined.

While a preferred embodiment has been designed to monitor beta emitting analyte levels in blood, the sensor of the invention can conceivably be used to measure any type of ionizing radiation in any fluid.

The fluid containing the analyte can be a gas, for example, air, respired air or the gases released in a fermentation process or cell culture process. The fluid can be a liquid, for example, a cell culture medium.

Examples of useful applications for the sensor of the present invention are pharmacokinetic studies, determination of vapor pressures, determination of reaction mechanisms, toxicology studies, clinical in vivo tracer diagnosis and clinical in vitro analysis.

Pharmacokinetic studies concern the quantitative study of the dynamics of xenobiotic disposition of drugs. This includes the processes of absorption, distribution, metabolism and excretion of either the parent compound or any metabolites. These studies involve the measurement of kinetic parameters such as biological half-life, renal clearance and apparent volume of distribution.

The sensitivity of the sensor of the present invention can be maintained when the diameter of the sensor is in the range of from about 50 micrometers ($\mu m$) to about 1000 $\mu m$. To be useful as an intravenous sensor in rats, a commonly used test animal, for example, a desirable diameter should range from about 400 $\mu m$ to about 600 $\mu m$.

DETAILED DESCRIPTION OF THE DRAWINGS

In FIG. 1 is shown a cross-section of an embodiment of the sensor of the present invention wherein the waveguide is an optical fiber 10 which is coupled to an electro-optical system, not shown, through a fiberoptic coupler 11, and comprises a fiber core 12, enclosed by fiber core cladding 13. A sheath 14, covers the optical fiber cladding and terminates at glue ring 15. The distal tip of the fiber core is enclosed in a semipermeable membrane 16, which is attached to the optical core at glue ring 17 and terminates at mirror plug 18, attached with glue ring 19. Within the enclosed space of the membrane and surrounding the fiber core is a scintillator 20, comprising scintillant particles.

Figure 2:
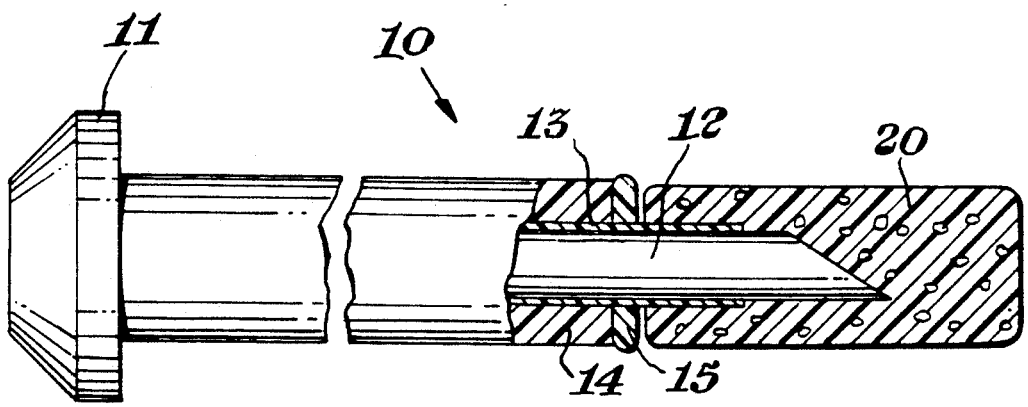
FIG. 2 depicts a cross-sectional view of a second embodiment of a sensor of the present invention.

In FIG. 2 is shown a cross-section of an embodiment of the sensor of the present invention wherein the waveguide is an optical fiber 10 which is coupled to an electro-optical system, not shown, through a fiberoptic coupler 11, and comprises a fiber core 12, enclosed by fiber core cladding 13. A sheath 14, covers the optical fiber cladding and terminates at glue ring 15. The distal tip of the fiber core is enclosed in an openly cellular scintillator 20.

EXAMPLE I

In Vitro Measurement of $^{14}$C-labelled Analyte in Rat Blood

The sensor of FIG. 1 was constructed from a 1 meter length of a SK-20 Super Eska (Mitsubishi Rayon, Tokyo, Japan) optical fiber 10 which comprised a poly(methyl methacrylate) core 12 with a fluorocarbon cladding 13. The sensor end was terminated with a fiberoptic coupler 11 which was manufactured by AMP (Harrisburg, PA) and sized to fit the above mentioned optical fiber. The fiber length, except for the distal end, was enclosed in a black tetrafluoroethylene sheath 14, terminating at silicone adhesive room temperature vulcanizing (RTV) glue ring 15. The sheath acted to exclude stray light.

The distal end of the sensor was prepared by first dipping the optical fiber into ethyl acetate, to strip the optical fiber core cladding 13 and sheath 14 from the fiber core 12. The distal tip was then cut, using a hot razor blade, at an acute angle of about 30°. A tubular polysulfone semipermeable membrane 16 having an inside diameter of 500 μm and an outside diameter of 550 μm was affixed to the distal fiber core tip using a RTV glue ring 17, leaving about 2 mm of the membrane extending past the angle cut tip of the fiber core. This volume was loosely packed with particles of anthracene as scintillator 20. The end of the membrane was terminated with a short length of Nichrome wire whose inside face has been polished to a mirror finish to form a reflecting mirror plug 18. This wire was sealed to the membrane with an RTV glue ring 19.

The sensor of FIG. 1 was connected to a longer (about 2 meters) 600 μm diameter silica quartz extension optical fiber via the fiberoptic coupler 11. The output from the extension fiber was focused through an imaging lens onto a FM 130 photomultiplier tube with a R-20 photocathode, (ITT, New York, N.Y.). The imaging lens assembly, extension fiber termination and photomultiplier tube were contained in a lightproof, thermoelectrically cooled (about −30° C.) container which is purged with dry air to prevent condensation. The output from the photomultiplier tube was amplified, processed and the resulting electronic pulse rate corresponding to the photon pulse rate from the sensor was measured using a photon counter. The output of the photon counter was related to the $^{14}$C activity of the sample using a calibration curve.

The $^{14}$C measurements were performed on unlabelled aqueous solutions and blood solutions of $^{14}$C labelled 1-methoxy-2-propanol. The $^{14}$C labelled solution was prepared from a stock sample whose activity was measured by adding 1 microliter (μl) of stock sample to 10 milliliters (ml) of ACS Cocktail scintillation fluid, (Amersham, Arlington Heights, Ill.). The sample was measured for radioactivity on a standard scintillation counter to yield an average activity of about 3.8 million disintegrations per minute per microliter (dpm/μl). An amount of 100 μl of the stock sample was added to 1.5 ml of water to produce the diluted stock solution (DSS). About nine ml of rat blood was extracted into heparinized tubes and the blood was divided into six aliquots, each containing about 1.5 ml of blood. Into the six blood samples was added, respectively, the following amounts of DSS (in μl): 250, 100, 50, 20, 4, and 2. The radioactivity of each of these samples was measured similarly to that described for the DSS. Experiments were performed in darkrooms and additional light shielding was placed around the sensor. Typically, background counts taken in unlabelled 1-methoxy-2-propanol were computed to be about 30 to about 100 counts per minute (cpm). The final count rate was calculated by subtracting the average background counts from the average labelled sample counts.

When a log-log plot was constructed of the sensor measured activity in cpm versus the actual or known activity in the six rat blood samples the bestfit line to the data had a slope of 0.98 over an activity range of from about 5,000 to 500,000 dpm/pl. The linearity of this curve which showed relatively little scatter indicating that the sensor of this example was stable over a wide range of activity. The data further shows that the sensor had a $^{14}$C sensitivity of about $7.1 \times 10^6$ cpm/dpm/μl/m$^3$

EXAMPLE II

In Vivo Measurement of $^{14}$C Activity in Pharmacokinetic Studies on Experimental Animals The sensor and methods of Example I are used to detect the concentration of a $^{14}$C-labelled analyte, salicylic acid-$^{14}$C in the hepatic-portal and peripheral circulation of a dog in order to determine the pharmacokinetic activity of the analyte. The sensor is implanted through a catheter using the cannulating techniques disclosed in Rheingold, et al., *Journal of Pharmaceutical Sciences* 71 (1982) 840–842. The real time measurement of $^{14}$C activity is representative of the kinetics of the drug.

In a similar manner, pharmacokinetic studies are performed on a monkey using venous catheterization and cannulating techniques disclosed in Wakeley, et al., *Behavior Research Methods & Instrumentation* 6 (1974) 329–331 and rabbit using cannulating techniques disclosed in Bazaral, et al., *Journal of Applied Physiology* 29 (1970) 113–114.

The results show that measured absorption rate, steady state concentration and elimination rate of salicylic acid in the blood corresponded to values measured using in vitro methods.

EXAMPLE III

In Vivo Pharmacokinetic Studies on Rats

The sensor of Example I is miniaturized to measure less than 500 μm in diameter and fitted into a twenty gauge needle. The sensor is implanted into Fisher Rats using the techniques disclosed in Harms, et al., *Journal of Applied Physiology* 36 (1973) 391–392.

The rats are anesthetized with methoxyfluorane or halothane. An incision is made over the right jugular vein in the shaved neck region. The surrounding tissue is dissected away from the vein and a hook and a 4-0 suture are placed under the vessel. A cannula is inserted and tied in place using the 4-0 suture. The cannula is also sutured to a segment of the shoulder muscle to assure anchorage of the cannula. After flushing with heparinized saline, the sensor is inserted through the cannula and tested for independent placement within the vessel. The throat incision is closed and the cannula is further secured to the animal's front shoulders using a 3-0 suture. The length of cannula with internalized optical sensor is connected to an electro-optical system.

The animal is given multiple doses with nonlabelled analyte and then given a single dose of a $^{14}C$ labelled analyte to measure the steady-state pharmacokinetic parameters of absorption rate, steady-state concentration and elimination rate of the analyte from the bloodstream. These parameters are measured by monitoring the concentration of $^{14}C$ in the bloodstream over approximately four biological half-lives of the analyte. This time amounts to about seventy-two hours or until greater than 90 percent of the $^{14}C$ labelled analyte has been eliminated.

The results indicate that the health of a rat is not compromised using this in vivo technique whereas in the event that blood samples are withdrawn from rats and used for in vitro analysis, the animal is usually not viable after 15 samples have been taken. This method gives superior results over a longer period of time while maintaining the health of the animal.

What is claimed is:

1. A sensor for determining the concentration of an ionizing radiation emitting analyte in a fluid comprising:
   (a) a scintillator having permeability to said fluid, said scintillator being effective for yielding a sensitivity to ionizing radiation above $2.5 \times 10^3$ counts per minute per disintegration per minute per microliter per cubic meter of scintillator ($cpm/dpm/\mu l/m3$); and
   (b) an optical waveguide in working relation with said scintillator to collect light photons generated by said scintillator in response to an ionizing radiation source.

2. The sensor of claim 1 wherein the sensor includes a permeable membrane surrounding the scintillator.

3. The sensor of claim 1 wherein the sensor includes a reflecting surface positioned with respect to the optical waveguide and the scintillator in a manner such that the intensity of light photons impinging on the waveguide is substantially increased.

4. The sensor of claim 1 wherein the scintillator is sensitive to beta emitting ionizing radiation.

5. The sensor of claim 1 wherein the sensor has a diameter of from about 50 to about 1000 micrometers.

6. The sensor of claim 1 wherein the sensor has a diameter of from about 400 to about 600 micrometers.

7. The sensor of claim 1 wherein the sensor includes a semipermeable membrane surrounding the scintillator.

8. The sensor of claim 7 wherein the semipermeable membrane is selected from the group consisting of cellulose acetate, polyvinylidene fluoride, polytetrafluoroethylene, copolymers of acrylonitrile/vinylpyrrolidone, polyamideimide, polysulfone, polyamide, hydrophilic polyolefin, copolymer of acrylonitrile/methallyl sulfonate, sulfonated polysulfone, silicone rubber, microporous polyolefin, polytetrafluoroethylene and combinations thereof.

9. The sensor of claim 8 wherein the semipermeable membrane is selected from the group consisting of cellulose acetate, polysulfone, sulfonated polysulfone, polyfluorocarbon and combinations thereof.

10. The sensor of claim 1 wherein the optical waveguide is an optical fiber.

11. The sensor of claim 10 wherein the scintillator is selected from the group consisting of organic crystal, organic plastic, inorganic crystal, inorganic amorphous solid and combinations thereof.

12. The sensor of claim 11 wherein the scintillator is selected from the group consisting of anthracene, picene, naphthacene, naphthalene, pentacene, hexacene, phenanthrene, fluoranthene, chrysens, pyrene, fluorene, carbazole, diphenylene oxide and combinations thereof.

13. The sensor of claim 1 wherein the scintillator is an openly cellular foam.

14. The sensor of claim 13 wherein the foam is a polymeric matrix in combination with at least one scintillator.

15. The sensor of claim 14 wherein the polymeric matrix is selected from the group consisting of poly(styrene), poly(vinyl toluene), poly(vinyl naphthalene), poly(vinyl anthracene), poly(methyl methacrylate) and the copolymers and blends thereof.

16. A method for determining the concentration of an ionizing radiation emitting analyte in a fluid medium, comprising the steps of:
   (A) inserting a sensor into the medium, wherein the sensor comprises:
      (a) a scintillator having a permeability to said fluid; and
      (b) an optical waveguide in working relation with said scintillator to collect light photons generated by said scintillator in response to an ionizing radiation source:
   (B) collecting the light photons from the scintillator through the waveguide:
   (C) measuring the number of the light photons and relating the measured number to a known standard to determine the concentration of the analyte in the fluid medium.

17. The method of claim 16 wherein the sensor further comprises a reflecting surface positioned with respect to the optical waveguide and the scintillator in a manner such that the intensity of light photons impinging on the waveguide is substantially increased.

18. The method of claim 16 wherein the optical waveguide is an optical fiber.

19. The method of claim 16 wherein the scintillator is selected from the group consisting of organic crystal, organic plastic, inorganic crystal, inorganic solid and composites thereof.

20. The method of claim 19 wherein the scintillator is selected from the group consisting of anthracene, picene, naphthacene, naphthalene, pentacene, hexacene, phenanthrene, fluoranthene, chrysene, pyrene, fluorene, carbazole, diphenylene oxide and combinations thereof.

21. The method of claim 16 wherein the scintillator is selected from the group consisting of anthracene, phenanthrene, fluoranthene, naphthacene, fluorene and carbazole.

22. The method of claim 16 wherein the analyte comprises a beta emitting compound.

23. The method of claim 16 wherein the analyte comprises a compound labelled with $^{14}C$.

24. The method of claim 16 wherein the sensor has a diameter of from about 50 to about 1000 micrometers.

25. The method of claim 16 wherein the sensor has a diameter of from about 400 to about 600 micrometers.

26. The method of claim 16 wherein the scintillator is in the form of an openly cellular foam.

27. The method of claim 26 wherein the foam comprises a polymeric matrix in combination with at least one scintillator wherein the polymeric matrix is selected from the group consisting of poly(styrene), poly(vinyl toluene), poly(vinyl naphthalene), poly(vinyl anthracene), poly(methyl methacrylate) and the copolymers and blends thereof.

28. The method of claim 16 wherein the sensor further comprises a semipermeable membrane enclosing the scintillator.

29. The method of claim 28 wherein the semipermeable membrane is selected from the group consisting of cellulose acetate, polyvinylidene fluoride, polytetrafluoroethylene, copolymers of acrylonitrile/vinylpyrrolidone, polyamideimide, polysulfone, polyamide, hydrophilic polyolefin, copolymer of acrylonitrile/methallyl sulfonate, sulfonated polysulfone, silicone rubber, microporous polyolefin, tetrafluoroethylene fluorocarbon and combinations thereof.

30. The method of claim 29 wherein the semipermeable membrane is selected from the group consisting of cellulose acetate, polysulfone, sulfonated polysulfone, polyfluorocarbon and combinations thereof.

* * * * *